United States Patent [19]

McKinzie et al.

[11] Patent Number: 5,391,379

[45] Date of Patent: * Feb. 21, 1995

[54] ACID SANITIZER COMPOSITION

[75] Inventors: Michael D. McKinzie; Murray W. Winicov, both of Kansas City, Mo.

[73] Assignee: West Agro, Inc., Kansas City, Mo.

[*] Notice: The portion of the term of this patent subsequent to Jul. 19, 2011 has been disclaimed.

[21] Appl. No.: 157,700

[22] Filed: Nov. 24, 1993

Related U.S. Application Data

[63] Continuation-in-part of Ser. No. 131,869, Oct. 5, 1993, Pat. No. 5,330,769, which is a continuation of Ser. No. 973,826, Nov. 9, 1992, abandoned.

[51] Int. Cl.6 .................. A61K 33/42; A61K 33/04; A61K 31/19; A61K 31/20
[52] U.S. Cl. ................... 424/605; 424/703; 514/557; 514/558; 252/106; 252/107
[58] Field of Search ............... 424/605, 703; 514/557, 514/558; 252/106, 107

[56] References Cited

U.S. PATENT DOCUMENTS 4,404,040 9/1983 Wang .................. 134/22.14

OTHER PUBLICATIONS

Federal Register vol. 55, No. 146, Jul. 30, 1990, p. 30983–Notices, Docket No. 90F–0217.

*Primary Examiner*—Raymond Henley, III
*Assistant Examiner*—T. J. Criares
*Attorney, Agent, or Firm*—Hovey, Williams, Timmons & Collins

[57] ABSTRACT

Fatty acid sanitizer concentrates and diluted final solutions are provided which include individual amounts of germicidally effective fatty acid, hydrotrope, strong acid selected from the group consisting of phosphoric and sulphuric acid sufficient to lower the pH of the final solutions to about 1–5, and a concentrate stabilizing weak acid component selected from the group consisting of propionic, butyric and valeric acids and mixtures thereof. The concentrate stabilizing component enhances the room and low temperature phase stability of the concentrates, even when used at very low levels typically ranging from 3.5%–15% by weight. Preferably, the fatty acid is a mixture of nonanoic and decanoic acids, whereas the strong acid is selected from the group consisting of orthophosphoric, sulfuric and mixtures thereof. Alternately, stable concentrates and use dilutions can be provided using undecylenic acid, either alone or in combination with other fatty acids.

15 Claims, No Drawings

ACID SANITIZER COMPOSITION

RELATED APPLICATION

This is a continuation-in-part of Application Ser. No. 08/131,869, filed Oct. 5, 1993, now U.S. Pat. No. 5,330,769, which is a continuation of application Ser. No. 07/973,826, filed Nov. 9, 1992, now abandoned.

BACKGROUND OF THE INVENTION

1. Field of the Invention

The present invention is broadly concerned with improved fatty acid sanitizer compositions in both concentrate and diluted forms which include a relatively low-cost stabilizing component therein giving the compositions enhanced stability, particularly at low temperatures. More particularly, the invention is concerned with such concentrates and diluted solutions which include an effective amount of a weak acid selected from the group consisting of propionic, butyric and valeric acids and mixtures thereof; use of such stabilizing components at relatively moderate levels materially increases the room and low temperature stability of the compositions.

2. Description of the Prior Art

A number of different sanitizing compositions have been proposed in the past for the control of potentially harmful microbial species such as gram-negative and gram-positive bacteria, e.g., *E. coli* and *S. aureus*. For example, compositions of this type may be used in the dairy industry for sanitizing milk-handling equipment and lines. As can be appreciated, such equipment must be routinely cleaned and sanitized to avoid the buildup of bacteria thereon which would contaminate the milk product.

Representative and effectively equivalent prior sanitizing compositions have included iodine (U.S. Pat. No. 3,650,965), or fatty acids (U.S. Pat. Nos. 3,867,300 and 4,404,040) as the primary bactericidal agents therein. Moreover, these compositions are generally sold to end users as concentrates, and are then diluted with a relatively large fraction of water to form final cleaning solutions.

A problem with certain of these prior compositions, and particularly the fatty acid-type sanitizers, stems from the fact that they have poor phase stability unless significant amounts of relatively expensive additives (e.g., citric acid) are employed. This in turn means that the cost of the sanitizers is increased, not in order to provide more effective germicidal activity, but simply to insure that the concentrates do not undergo phase separation at room or low temperatures.

SUMMARY OF THE INVENTION

The present invention overcomes the problems outlined above, and provides greatly improved acid sanitizer concentrates and diluted final solutions which employ as the stabilizing component thereof relatively minor amounts of a weak acid selected from the group consisting of propionic, butyric and valeric (by which is meant to include both valeric and isovaleric) acids and mixtures thereof. These acids are well known: propionic (CAS #79-09-04); butyric (CAS #107-92-6); valeric (CAS #109-52-4); isovaleric (CAS #503-74-2).

Broadly speaking, diluted acid sanitizer concentrates in accordance with the invention include individual amounts of germicidally effective fatty acid, hydrotropesolubilizer, strong acid, a weak acid stabilizing component and water. Generally, the weak acid stabilizing component should be present at a level of at least about 2% by weight in the concentrates, more preferably from about 3.5-15% by weight, and most preferably about 10% by weight. In terms of the diluted final solutions, the weak acid stabilizing component should be present at a level of from about 30-500 ppm, more preferably from about 40-240 ppm, and most preferably about 150-160 ppm. The single most preferred stabilizing component is propionic acid, inasmuch as this component gives the least offensive odor. However, excellent stabilizing results can be obtained (with even smaller total quantities of stabilizer) by employing mixtures of the indicated acids, such as propionic and butyric.

The fatty acid component of the concentrates is advantageously selected from the aliphatic $C_6$-$C_{11}$ fatty acids, and particularly nonanoic (CAS #112-05-0) and decanoic (CAS #334-48-5) acids, and mixtures thereof. These fatty acids are normally present at a level of from about 2%-12% by weight depending upon the germicidal activity required in the final dilute solutions, and most preferably about 6% by weight. Particularly preferred concentrates contain 3% by weight nonanoic acid and 3% by weight decanoic acid. Again, in the context of the diluted solutions, the fatty acid content thereof should be at least about 50 ppm, more preferably from about 60-125 ppm, and most preferably about 90-100 ppm. Where the most preferred concentrates are diluted, these dilute final solutions should contain about 45-50 ppm nonanoic acid, and about 45-50 ppm decanoic acid. In alternative forms, a fatty acid component present at a level of up to about 3.5% by weight in the concentrate can be provided, wherein the fatty acid component contains respective minor amounts of decanoic and undecylenic acids.

The hydrotrope component of the compositions can be nonionic or anionic but is preferably the latter. Surfactants selected from the group consisting of the alkane sulfonates (such as alkali metal alkane sulfonates) and the corresponding disulfonates are especially useful. The most preferred anionic hydrotrope is a mixture of sodium 1-octane sulfonate and sodium 1,2-octane disulfonate. In the concentrates, the hydrotrope should be present at a level of from about 5%-20% by weight, more preferably from about 5%-15% by weight and most preferably from about 8%-12% by weight; the diluted final solution should correspondingly contain from about 75-320 ppm, more preferably from about 75-235 ppm, and most preferably from about 125-190 ppm hydrotrope.

The strong acid component of the compositions provides the desired low pH in the final solutions of from about 1-5, and preferably from about 2.5-4. The strong acid is advantageously taken from the group consisting of phosphoric, sulfuric and mixtures and thereof, and suitable compositions can be made using only phosphoric acid, or a combination of these two acids. The strong acid is normally present at a level of from about 5%-40% by weight in the concentrates, and more preferably from about 10%-30% by weight. In the diluted final solutions, the strong acid is present at a level of from about 75-625 ppm, and more preferably from about 150-470 ppm.

The balance of the concentrates and final solutions is provided by water. Thus, in the concentrates, the water content is from about 30%-80% by weight, whereas in the final solutions, the water is in excess of about 99% by weight.

DETAILED DESCRIPTION OF THE PREFERRED EMBODIMENTS

The most preferred dilutable acid sanitizer concentrates in accordance with the invention comprise, and preferably consist essentially of, the following ingredients, wherein all percentages are approximate and on a weight basis:
- 3% nonanoic acid
- 3% decanoic acid
- 8%–10% of a mixture of sodium 1-octane sulfonate and sodium 1,2-octane disulfonate
- 8%–30% by weight of strong acid selected from the group consisting of orthophosphoric, sulfuric and mixtures thereof
- 10% propionic acid
- water balance This preferred concentrate when diluted 1 fluid ounce:6 gallons (1:768) with water gives a final solution adapted for surface cleaning/sanitizing made up of the following components, wherein all percentages are approximate and on a weight basis:
- 47 ppm nonanoic acid
- 47 ppm decanoic acid
- 125–160 ppm of a mixture of sodium octane sulfonate and sodium octane disulfonate
- 125–470 ppm by weight of strong acid selected from the group consisting of orthophosphoric, sulfuric and mixtures thereof
- 160 ppm propionic acid
- water balance The above final composition gives excellent microbial activity when contacted with hard surfaces, and under appropriate time and temperature conditions, will substantially completely eliminate undesired bacteria. For example, kills greater than 99.999% for both $E.\ coli$ and $S.\ aureus$ can be readily obtained under the standard conditions of AOAC Germicidal and Detergent Sanitizer test described in the *Official Methods of Analysis of the AOAC,* Fourteenth Edition, Ch. 4, Disinfectants paragraphs 4.020–4.029, incorporated by reference herein.

The presence of strong acid in the compositions serves to lower the pH of final dilute solutions within the range of about 1–5. In this respect, the strong acid component is the only material ingredient providing this degree of pH lowering. That is, the propionic acid has virtually no effect upon pH of the final solutions, and hard water-diluted concentrates with the strong acid component eliminated have pHs on the order of 6. Two particularly preferred concentrate compositions in accordance with the invention contain, respectively, about 28% by weight orthophosphoric acid, and a mixture of 8.5% by weight orthophosphoric acid and 9.8% by weight sulfuric acid.

The preferred hydrotrope set forth in the foregoing ingredients can be obtained from commercial sources. For example, the hydrotrope may be obtained from Stepan Chemical Co. as its Bio-Terge PAS-8S product (CAS #5324-84-5). This anionic surfactant is a mixture of sodium 1-octane sulfonate and sodium 1,2-octane disulfonate, and, when used at a level of 30% by weight in the concentrates of the present invention, provides about 6%–7.5% by weight of the monosulfonate, and from about 2%–2.5% by weight of the disulfonate. A very similar alkyl sulfonate is also sold by Witco Chemical Co. as "Witconate NAS-8," (CAS #5324-84-5).

EXAMPLE 1

A test was undertaken to determine the effect of use of propionic, butyric and valeric acids in fatty acid hard surface sanitizer concentrates, insofar as the solubility, homogeneity, and compatibility of these sanitizers is concerned. In each case, the respective sanitizer samples were prepared in small quantities (10 g, and in some cases 4 g) by simple mixing of the ingredients in 16 mm—125 mm screw cap culture tubes. The ingredients were typically added in the following order: water, strong acid(s), hydrotrope-solubilizer, weak acid(s) and fatty acid(s). In cases where the weak acid was a solid, such as citric acid, it was added first to the water in order to facilitate dissolution. A Thermolyne "Maxi Mix II" vortex mixer was used to thoroughly mix the ingredients of each sample in a corresponding tube.

The samples were then allowed to stand overnight at normal laboratory temperature (23° C.–27° C.), and were then observed for any signs of phase instability such as separation into two or more liquid phases or the presence of solid precipitate. Samples showing no stability problems at room temperature were then placed in a refrigerator maintained at a temperature of from about 0° C.–1° C. The samples were then observed, between 24 and 48 hours later, for any signs of phase instability. The samples were deemed unstable at low temperature if they did not remain as single phase, homogeneous liquids.

The following tables set forth the compositions tested and the results obtained from various fatty acid hard surface sanitizer compositions made in accordance with the present invention, and certain conventional sanitizer compositions. The tables list the ingredients, in units of % by weight, for each test composition, where the balance to 100% of each sample was water. In these tables, "SEP" refers to separation into two or more phases, "FR" refers to a totally frozen sample, "PTFR" refers to a partially frozen sample, "SLSH" refers to a slushy sample, "CDS" refers to a sample giving the appearance of curds, and "CRST" refers to the appearance of crystals in the sample. All of these conditions are deemed deficient and indicative of failure whereas the "OK" designation indicates an acceptable sample.

TABLE 1

| Sample # | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| \multicolumn{16}{c}{LOW TEMPERATURE STABILITY} | | | | | | | | | | | | | | | |
| 98% Octane Sulfonate | 12 | 12 | 12 | 12 | 12 | 12 | 12 | 12 | 12 | 12 | 12 | 12 | 12 | 12 | 12 |
| H$_3$PO$_4$ (75%) | 30 | 30 | 30 | 30 | 30 | 30 | 30 | 30 | 30 | 30 | 30 | 30 | 30 | 30 | 30 |
| Octanoic Acid | 4.8 | 4.8 | 4.8 | 4.8 | 4.8 | 4.8 | 4.8 | 4.8 | 4.8 | 4.8 | 4.8 | 4.8 | 4.8 | 4.8 | 4.8 |
| Decanoic Acid | 3.2 | 3.2 | 3.2 | 3.2 | 3.2 | 3.2 | 3.2 | 3.2 | 3.2 | 3.2 | 3.2 | 3.2 | 3.2 | 3.2 | 3.2 |
| Citric Acid | 22.5 | — | 11.25 | 16.875 | — | — | — | — | — | — | — | — | — | — | — |
| Propionic Acid | — | — | — | — | 5 | 10 | — | — | — | 3 | 5.25 | 6.5 | — | — | — |
| Butyric Acid | — | — | — | — | — | — | 5 | 10 | — | — | 3 | 1.5 | 1.5 | — | — |
| Valeric Acid | — | — | — | — | — | — | — | — | 5 | 10 | — | — | — | — | — |

TABLE 1-continued

| Sample # | LOW TEMPERATURE STABILITY | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Fumaric Acid | — | — | — | — | — | — | — | — | — | — | — | — | — | 5 | — |
| Maleic Acid | — | — | — | — | — | — | — | — | — | — | — | — | — | — | 20 |
| R.T. Stability | OK | SEP | SEP | OK | OK | OK | OK | OK | SEP | OK | OK | OK | OK | SEP | OK |
| 0° C. Stability | OK | — | — | SEP | SEP | OK | SEP | OK | — | SEP | SEP | OK | OK | — | FR |

TABLE 2

| Sample # | 16 | 17 | 18 | 19 | 20 | 21 | 22 | 23 | 24 | 25 | 26 | 27 |
|---|---|---|---|---|---|---|---|---|---|---|---|---|
| Bioterge PAS-8S | 26.7 | 22.9 | 20.0 | 17.8 | 16.0 | 8.0 | 26.7 | 22.9 | 20.0 | 17.8 | 16.0 | 8.0 |
| 98% Octane Sulfonate | 2.66 | 3.98 | 5.00 | 5.78 | 6.40 | 9.20 | 2.66 | 3.98 | 5.00 | 5.78 | 6.40 | 9.20 |
| $H_3P_4$ (85%) | 26.5 | 26.5 | 26.5 | 26.5 | 26.5 | 26.5 | 33 | 33 | 33 | 33 | 33 | 33 |
| Octanoic Acid | 6.5 | 6.5 | 6.5 | 6.5 | 6.5 | 6.5 | 6.5 | 6.5 | 6.5 | 6.5 | 6.5 | 6.5 |
| Decanoic Acid | 3 | 3 | 3 | 3 | 3 | 3 | 3 | 3 | 3 | 3 | 3 | 3 |
| Citric Acid | 20 | 20 | 20 | 20 | 20 | 20 | — | — | — | — | — | — |
| Propionic Acid | — | — | — | — | — | — | 10 | 10 | 10 | 10 | 10 | 10 |
| R.T. Stability | OK | OK | OK | OK | OK | OK | OK | OK | OK | OK | OK | OK |
| 0° C. Stability | SEP | FR | FR | FR | FR | PTFR | OK | OK | OK | OK | OK | OK |

TABLE 3

| Sample # | 28 | 29 | 30 | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|---|---|---|
| Bioterge PAS-8S | 35 | 35 | 30 | 30 | 30 | 30 | 30 | 30 | 30 | 30 | 30 | 30 | 30 | 30 | 30 | 30 | 30 | 30 |
| $H_3PO_4$ (85%) | 33 | 33 | 10 | 10 | 33 | 33 | 33 | 33 | 33 | 33 | 33 | 33 | 10 | 10 | 10 | 10 | 10 | 10 |
| $H_2SO_4$ (98%) | — | — | 10 | 10 | — | — | — | — | — | — | — | — | 10 | 10 | 10 | 10 | 10 | 10 |
| Decanoic Acid | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 |
| Propionic Acid | 10 | 15 | 14 | 16 | 16 | 17.5 | 19 | 15 | 20 | — | — | — | — | — | — | — | — | — |
| Acetic Acid | — | — | — | — | — | — | — | — | — | 20 | 25 | 30 | — | — | — | — | — | — |
| Valeric Acid | — | — | — | — | — | — | — | — | — | — | — | — | 3 | 4 | 5 | — | — | — |
| i-Valeric Acid | — | — | — | — | — | — | — | — | — | — | — | — | — | — | — | 4 | 5 | 6 |
| R. T. Stability | OK | OK | OK | OK | OK | OK | OK | OK | OK | OK | OK | OK | OK | OK | OK | OK | OK | OK |
| 0° C. Stability | FR | OK | FR | OK | OK | OK | OK | SLSH | OK | FR | FR | FR | FR | OK | OK | FR | OK | OK |

TABLE 4

| Sample # | 46 | 47 | 48 | 49 | 50 | 51 | 52 | 53 | 54 | 55 |
|---|---|---|---|---|---|---|---|---|---|---|
| BiotergePAS-8S | 30 | 35 | 30 | 40 | 30 | 30 | 40 | 30 | 30 | 35 |
| $H_3PO_4$ (85%) | 26.5 | 26.5 | 26.5 | 26.5 | 26.5 | 10 | 10 | 10 | 10 | 10 |
| $H_2SO_4$ (98%) | — | — | — | — | — | 10 | 10 | 10 | 10 | 10 |
| Octanoic Acid | 6.5 | 6.5 | 6.5 | 6.5 | 6.5 | 6.5 | 6.5 | 6.5 | 6.5 | 6.5 |
| Decanoic Acid | 3 | 3 | 3 | 3 | 3 | 3 | 3 | 3 | 3 | 3 |
| Citric Acid | 20 | 20 | 10 | 20 | 20 | 20 | 20 | — | — | — |
| Propionic Acid | — | — | — | — | — | — | — | 5 | 10 | 5 |
| R. T. Stability | SEP | OK | SEP | OK | SEP | SEP | OK | OK | OK | OK |
| 0° C. Stability | — | FR | — | FR | — | — | SEP | OK | OK | OK |

| Sample # | 56 | 57 | 58 | 59 | 60 | 61 | 62 | 63 | 64 | 65 |
|---|---|---|---|---|---|---|---|---|---|---|
| BiotergePAS-8S | 40 | 45 | 50 | 40 | 40 | 30 | 30 | 30 | 35 | 35 |
| $H_3PO_4$ (85%) | 10 | 10 | 10 | 33 | 33 | 33 | 33 | 33 | 33 | 33 |
| $H_2SO_4$ (98%) | 10 | 10 | 10 | — | — | — | — | — | — | — |
| Octanoic Acid | 6.5 | 6.5 | 6.5 | 6.5 | 6.5 | 6.5 | 6.5 | 6.5 | 6.5 | 6.5 |
| Decanoic Acid | 3 | 3 | 3 | 3 | 3 | 3 | 3 | 3 | 3 | 3 |
| Citric Acid | — | — | — | — | — | — | — | — | — | — |
| Propionic Acid | 5 | 5 | 5 | 10 | 15 | 5 | 10 | 15 | 5 | 10 |
| R. T. Stability | OK | OK | OK | OK | OK | OK | OK | OK | OK | OK |
| 0° C. Stability | OK | OK | OK | CDS | OK | OK | OK | SEP | CDS | CDS |

TABLE 5

| Sample # | 66 | 67 | 68 | 69 | 70 | 71 | 72 | 73 | 74 |
|---|---|---|---|---|---|---|---|---|---|
| BiotergePAS-8S | 30 | 35 | 35 | 35 | 35 | 30 | 30 | 30 | 30 |
| $H_3PO_4$ (85%) | 30 | 30 | 30 | 30 | 30 | 10 | 10 | 33 | 33 |
| $H_2SO_4$ (98%) | — | — | — | — | — | 10 | 10 | — | — |
| Nonanoic Acid | 3 | 3 | 3 | 3 | 3 | 3 | 3 | 3 | 3 |
| Decanoic Acid | 3 | 3 | 3 | 3 | 3 | 3 | 3 | 3 | 3 |
| Citric Acid | 20 | 20 | 20 | 20 | 15 | 5 | 10 | 5 | 10 |
| Propionic Acid | 5 | 5 | 7.5 | 9 | 10 | — | — | — | — |
| R.T. Stability | SEP | OK | OK | OK | OK | OK | OK | OK | OK |
| 0° C. Stability | — | FR | SEP | SEP | SEP | FR | FR | FR | FR |

TABLE 6

| Sample # | 75 | 76 | 77 | 78 | 79 | 80 | 81 | 82 | 83 | 84 |
|---|---|---|---|---|---|---|---|---|---|---|
| BiotergePAS-8S | 30 | 30 | 30 | 30 | 30 | 30 | 30 | 30 | 30 | 30 |
| $H_3PO_4$ (85%) | 33 | 33 | 33 | 10 | 10 | 10 | 10 | 10 | 33 | 33 |
| $H_2SO_4$ (98%) | — | — | — | 10 | 10 | 10 | 10 | 10 | — | — |
| Nonanoic Acid | 3 | 3 | 3 | 3 | 3 | 3 | 3 | 3 | 3 | 3 |
| Decanoic Acid | 3 | 3 | 3 | 3 | 3 | 3 | 3 | 3 | 3 | 3 |
| Acetic Acid | 5 | 10 | 15 | 5 | 10 | 15 | — | — | — | — |
| Propionic Acid | — | — | — | — | — | — | 10 | 5 | 5 | 10 |
| R.T. Stability | OK | OK | OK | OK | OK | OK | OK | OK | OK | OK |
| 0° C. Stability | FR | FR | FR | FR | SLSH | SLSH | OK | FR | FR | OK |

TABLE 7

| Sample # | 85 | 86 | 87 | 88 | 89 | 90 | 91 | 92 | 93 | 94 | 95 | 96 |
|---|---|---|---|---|---|---|---|---|---|---|---|---|
| BiotergePAS-8S | 30 | 30 | 30 | 30 | 30 | 30 | 30 | 30 | 30 | 30 | 30 | 30 |
| $H_3PO_4$ (85%) | 10 | 10 | 33 | 33 | 10 | 33 | 10 | 33 | 10 | 10 | 10 | 10 |
| $H_2SO_4$ (98%) | 10 | 10 | — | — | 10 | — | 10 | — | 10 | 10 | 10 | 10 |
| Nonanoic Acid | 3 | 3 | 3 | 3 | 3 | 3 | 3 | 3 | 3 | 3 | 3 | 3 |
| Decanoic Acid | 3 | 3 | 3 | 3 | 3 | 3 | 3 | 3 | 3 | 3 | 3 | 3 |
| Propionic Acid | — | — | — | — | — | 5 | 5 | 2.5 | 2.5 | 3 | — | — |
| Butyric Acid | 2.5 | 5 | 5 | 2.5 | 1 | 1 | 1 | 1 | 1 | 1 | — | — |
| Valeric Acid | — | — | — | — | — | — | — | — | — | — | 2.5 | 5 |
| i-Valeric Acid | — | — | — | — | — | — | — | — | — | — | — | — |
| Hexanoic Acid | — | — | — | — | — | — | — | — | — | — | — | — |
| Heptanoic Acid | — | — | — | — | — | — | — | — | — | — | — | — |
| R.T. Stability | OK | OK | OK | OK | OK | OK | OK | OK | OK | OK | OK | SEP |
| 0° C. Stability | OK | OK | OK | SEP | SLSH | OK | OK | OK | CRST | OK | SEP | — |

| Sample # | 97 | 98 | 99 | 100 | 101 | 102 | 103 | 104 | 105 | 106 | 107 | 108 |
|---|---|---|---|---|---|---|---|---|---|---|---|---|
| BiotergePAS-8S | 30 | 30 | 30 | 30 | 30 | 30 | 30 | 30 | 30 | 30 | 30 | 30 |
| $H_3PO_4$ (85%) | 33 | 33 | 33 | 33 | 33 | 10 | 10 | 10 | 33 | 33 | 33 | 33 |
| $H_2SO_4$ (98%) | — | — | — | — | — | 10 | 10 | 10 | — | — | — | — |
| Nonanoic Acid | 3 | 3 | 3 | 3 | 3 | 3 | 3 | 3 | 3 | 3 | 3 | 3 |
| Decanoic Acid | 3 | 3 | 3 | 3 | 3 | 3 | 3 | 3 | 3 | 3 | 3 | 3 |
| Propionic Acid | — | — | — | — | 3 | — | — | 3 | — | — | — | — |
| Butyric Acid | — | — | — | — | — | — | — | — | — | — | — | — |
| Valeric Acid | 5 | 2.5 | — | — | — | — | — | — | — | — | — | — |
| i-Valeric Acid | — | — | 1 | 2.5 | 1 | 1 | 2.5 | 1 | — | — | — | — |
| Hexanoic Acid | — | — | — | — | — | — | — | — | 2.5 | 5 | — | — |
| Heptanoic Acid | — | — | — | — | — | — | — | — | — | — | 2.5 | 5 |
| R.T. Stability | OK | OK | SEP | OK | OK | OK | OK | OK | SEP | SEP | SEP | SEP |
| 0° C. Stability | OK | SEP | — | SEP | CRST | SEP | SEP | OK | — | — | — | — |

Referring first to Table 1, it can be seen that a sanitizer containing 4.8% by weight octanoic acid and 3.2% by weight decanoic acid has appropriate stability if a large amount (22.5% by weight) citric acid is employed. However, elimination of the citric acid or reduction in the amounts thereof, yields unstable sanitizers (samples #1–4). This is to be contrasted with samples #6 and 8, wherein 10% by weight of propionic or butyric acid gives a stable system. Thus, less than half the amount of the acids of the invention can be used, in lieu of the amount of citric acid needed. The total amount of weak acids can be even further lowered by using a combination of propionic and butyric acids (samples #12–13). Finally, fumaric and maleic acids were shown to be ineffective as system stabilizers (samples #14–15).

Table 2 (6.5% octanoic/3% decanoic acid samples) demonstrates that use of 20% citric acid is ineffective in achieving stable compositions, even when varying amounts of the mono and disulfonate are used (samples #16–21). However, comparative samples #22–27 each containing 10% by weight propionic acid, are stable. This further confirms that significantly more citric acid is required, as compared with the acids of the invention. This represents a significant commercial advantage in that the present-day price of citric acid is approximately $.80 per pound whereas the price for propionic acid is presently about $.40 per pound.

Table 3 (2.5% decanoic acid samples) represents another series of tests and demonstrates that compositions can be made using a combination of strong acids, in this case phosphoric and sulfuric; and that such compositions can be stabilized with appropriate amounts of the acids of the invention. For example, sample #41 demonstrates that a very minor amount of valeric acid (4% by weight) can be used to good effect. Similarly, small amounts of isovaleric acid (i-valeric acid) are also effective (samples #44–45). Finally, as depicted with samples #37–39, even significant amounts of acetic acid failed to give a stable composition.

Table 4 (6.5% octanoic/3% decanoic acid samples) provides further confirming evidence and shows that with this system, 5% by weight propionic acid is more effective than 20% by weight citric acid (samples #53, 55–58 and 61 versus samples #46–52).

All of the samples of Table 5 (all samples of Tables 5–7 had 3% nonanoic/3% decanoic fatty acids therein) failed, inasmuch as all these samples contained from between 5%–20% by weight citric acid. These failures resulted even though from 5%–10% by weight propionic acid was used in combination with the citric acid. This establishes that the propionic acid functions in a superior manner as compared with citric acid, and the two are not additive in effect.

Table 6 illustrates that in compositions containing a mixture of nonanoic and decanoic acids as the fatty acid component, acetic acid is ineffective, but that 10% by weight of propionic acid therein gives stable systems (samples #75–80 versus samples #81 and 84).

Table 7 records the results from a series of tests using various combinations of strong acid and weak acids, and confirms that a relatively small amount of butyric acid (2.5% by weight) gives a stable product (sample #85) and that a combination of 2.5% by weight propionic acid and 1% by weight butyric acid also gives a stable system (sample #92).

EXAMPLE 2

A preferred concentrate in accordance with the invention (sample #81, Table 6) was tested to determine the amount of foam generated in a laboratory test. The concentrate was diluted at a ratio of 1 fluid ounce concentrate per 6 gallons of 500 ppm AOAC synthetic hard water to provide a final dilute solution. The dilute solution was then tested in triplicate as set forth below.

Specifically, 300 milliliters of the dilute solution (at room temperature) was placed in a conventional, upright, open-top, 1000 milliliter graduated cylinder. A spherical alumina sparging device (AX536, Norton Co., Industrial Ceramics Div., Worcester, Mass.), soaked at least 4 hours in the dilute solution, was used for foam generation. This sparger is specified in a standard dynamic foam test (ASTM #D892-89), and was attached to a line connected with a source of pressurized gas (nitrogen). The sparger with tubing attached was lowered into the solution in the graduated cylinder, and seated adjacent the bottom of the latter. The flow of gas through the line and sparger was adjusted to a rate of 2 liter/min., and was then allowed to pass into the solution for a period of 15 seconds. At the end of the 15 second period, the total amount of foam present in the cylinder was measured by noting the uppermost foam level and subtracting therefrom the bottom level of the foam. The following results were recorded:

| Run # | Upper Foam Level (ml) | Bottom Foam Level (ml) | Total Foam (ml) |
|---|---|---|---|
| 1 | 610 | 100 | 510 |
| 2 | 610 | 80 | 530 |
| 3 | 610 | 80 | 530 |

EXAMPLE 3

In this Example, stable compositions making use of $C_{11}$ fatty acid (undecylenic) are illustrated. The compositions were prepared as set forth in Example 1, and included the following ingredients on a percent by weight basis. The compositions were also tested for room temperature and 0° C. stability, these results are set forth below:

TABLE 8

| Sample # | 109 | 110 |
|---|---|---|
| BioTerge PS-8S | 30 | 30 |
| Phosphoric Acid (85%) | 33 | 33 |
| Decanoic Acid | 2.0 | 1.5 |
| Undecylenic Acid | 1.5 | 2.0 |
| Propionic Acid | 10 | 10 |
| Water | 23.5 | 23.5 |
| R.T. Stability | OK | OK |
| 0° Stability | OK | OK |

EXAMPLE 4

The following Example demonstrates that nonionic surfactants (Igepal CO-887, Pluronic P-85 and Pluronic P-65) can be used to produce acid sanitizers in accordance with the invention. These compositions were prepared as set forth in Example 1 and included the following ingredients on a percent by weight basis. The compositions had acceptable room temperature stabilities.

TABLE 9

| Sample # | 111 | 112 |
|---|---|---|
| Igepal CO-887 | 15 | — |
| Pluronic P-85 | — | 10 |
| Pluronic P-65 | — | 10 |
| Sulfuric Acid (96%) | 10 | 10 |
| Phosphoric Acid (85%) | 10 | 10 |
| Propionic Acid | 10 | 10 |
| Decanoic Acid | 3 | 3 |
| Nonanoic Acid | 3 | 3 |
| Water | 49 | 44 |

We claim:

1. An aqueous, dilutable acid sanitizer concentrate composition comprising individual amounts of water, from about 2–12% by weight of an aliphatic $C_6$–$C_{11}$ germicidally effective fatty acid, from about 5–20% by weight of hydrotrope-solubilizer selected from the group consisting of nonionic and anionic hydrotrope-solubilizers, from about 5–40% by weight of a strong acid selected from the group consisting of phosphoric and sulfuric acids and mixtures thereof, and a component for giving the composition enhanced stability, said stabilizing component comprising an effective amount of from about 3.5–15% by weight of a weak acid selected from the group consisting of propionic, butyric and valeric acids and mixtures thereof, said composition, when diluted in water to form a use solution having a pH of from about 1–5.

2. The composition of claim 1, said stabilizing component being present at a level of about 10% by weight.

3. The composition of claim 1, said stabilizing component being propionic acid.

4. The composition of claim 1, said stabilizing component being a mixture of said acids.

5. The composition of claim 1, said fatty acid being selected from the group consisting of nonanoic, decanoic, undecylenic fatty acids and mixtures thereof.

6. The composition of claim 1, said fatty acid being present at a level of about 6% by weight.

7. The composition of claim 1, said hydrotrope-solubilizer comprising sodium 1-octane sulfonate and sodium 1,2-octane disulfonate.

8. The composition of claim 1, said level of hydrotrope-solubilizer being from about 5%–15% by weight.

9. The composition of claim 1, said strong acid being phosphoric acid.

10. The composition of claim 1, said strong acid being a mixture of phosphoric and sulfuric acid.

11. The composition of claim 1, said strong acid comprising about 8.5% by weight orthophosphoric acid and about 9.8% by weight sulfuric acid.

12. The composition of claim 1, said acid comprising about 28% by weight orthophosphoric acid.

13. The composition of claim 1, said hydrotrope-solubilizer being selected from the group consisting of the alkane sulfonates and disulfonates.

14. A dilutable acid sanitizer concentrate composition comprising:
  about 3.5% by weight of a fatty acid component comprising respective amounts of decanoic acid and undecylenic acid;
  from about 8–10% by weight of a mixture of sodium octane sulfonate and sodium octane disulfonate;

from about 8–30% by weight of a strong acid selected from the group consisting of orthophosphoric, sulfuric and mixtures thereof;

a component for giving the composition enhanced stability and comprising about 10% by weight of propionic acid; and the balance of said composition up to 100% by weight being water.

15. A dilutable acid sanitizer concentrate composition consisting essentially of:

about 3.5% by weight of a fatty acid component comprising respective amounts of decanoic acid and undecylenic acid;

from about 8–10% by weight of a mixture of sodium octane sulfonate and sodium octane disulfonate;

from about 8–30% by weight of a strong acid selected from the group consisting of orthophosphoric, sulfuric and mixtures thereof;

a component for giving the composition enhanced stability and comprising about 10% by weight of propionic acid; and the balance of said composition up to 100% by weight being water.

* * * * *